United States Patent
Yoshii et al.

(10) Patent No.: US 7,307,157 B2
(45) Date of Patent: Dec. 11, 2007

(54) PROCESS FOR PRODUCING CHITIN DERIVATIVES AND/OR CHITOSAN DERIVATIVES HAVING A CROSSLINKED STRUCTURE

(75) Inventors: Fumio Yoshii, Takasaki (JP); Naotsugu Nagasawa, Takasaki (JP); Tamikazu Kume, Takasaki (JP); Hiroshi Mitomo, Kiryu (JP)

(73) Assignee: Japan Atomic Energy Research Institute, Tokyo (JP)

( * ) Notice: Subject to any disclaimer, the term of this patent is extended or adjusted under 35 U.S.C. 154(b) by 0 days.

(21) Appl. No.: 11/028,203

(22) Filed: Jan. 4, 2005

(65) Prior Publication Data

US 2005/0113773 A1    May 26, 2005

Related U.S. Application Data

(63) Continuation of application No. 10/305,108, filed on Nov. 27, 2002, now abandoned.

(30) Foreign Application Priority Data

Nov. 28, 2001  (JP) .............................. 2001-362131

(51) Int. Cl.
C08B 37/08 (2006.01)
C07H 1/00 (2006.01)
A01N 43/04 (2006.01)

(52) U.S. Cl. ........................... 536/20; 536/124; 514/55
(58) Field of Classification Search ................. 536/20, 536/124; 514/55
See application file for complete search history.

(56) References Cited

U.S. PATENT DOCUMENTS

| | | | |
|---|---|---|---|
| 4,956,350 A | 9/1990 | Mosbey | |
| 5,462,976 A | 10/1995 | Matsuda et al. | |
| 6,124,273 A | 9/2000 | Drohan et al. | |
| 6,566,345 B2 * | 5/2003 | Miller et al. | 514/54 |
| 6,806,260 B1 * | 10/2004 | Hirofumi et al. | 514/55 |

FOREIGN PATENT DOCUMENTS

JP             56094322 A        7/1981

* cited by examiner

Primary Examiner—Shaojia Anna Jiang
Assistant Examiner—Everett White

(57) ABSTRACT

A process for producing a chitin derivative and/or a chitosan derivative that have a crosslinked structure, which comprises irradiating a paste of a mixture consisting of 100 parts by weight of a chitin derivative and/or a chitosan derivative and 3~1,000 parts by weight of purified water.

4 Claims, 1 Drawing Sheet

(a)　　　　　　(b)　　　　　　(c)

PROCESS FOR PRODUCING CHITIN DERIVATIVES AND/OR CHITOSAN DERIVATIVES HAVING A CROSSLINKED STRUCTURE

This application claims the benefit under 35 U.S.C. § 120 and 119(a) of prior filed U.S. application Ser. No. 10/305,108, filed Nov. 27, 2002 now abandoned, the entirety of which is hereby incorporated by reference and foreign priority of Japan application no. 362131/Japan filed Nov. 28, 2001.

BACKGROUND OF THE INVENTION

This invention relates to a process for producing chitin derivatives and/or chitosan derivatives with a crosslinked structure by adding purified water to chitin derivatives and/or chitosan derivatives, kneading the mixture well and applying an ionizing radiation to the kneaded mixture. The chitin derivatives having a crosslinked structure are hydrogels and the chitosan derivatives having a crosslinked structure are hydrogels having antimicrobial activity.

Hydrogels can hold a large amount of water within the three-dimensional network structure generated by crosslinking with radiation. The retained water will not seep out under slight pressure. Such hydrogels are already in use as disposable diapers and as humectants in cosmetics.

Carboxymethyl-chitin (CM-chitin) and carboxymethyl-chitosan (CM-chitosan), if they are irradiated in either a solid form or as a dilute ($\leqq 5\%$) aqueous solution, preferentially undergo decomposition and no hydrogels will form. If they are irradiated in a concentrated paste form (that will not flow out if the container is tilted), a crosslinked structure can be introduced and the resulting gel will absorb water upon immersion in it to become a hydrogel. In the case of a CM-chitosan hydrogel, it has been found to have a new feature, antimicrobial activity, in spite of it being a hydrogel.

Hydrogels can be easily obtained by applying an ionizing radiation to aqueous solutions of polyethylene oxides, poly(vinyl alcohol), polyacrylamides, polyvinylpyrrolidone, etc. Being capable of absorbing and holding a large amount of water, hydrogels are used in medical and cosmetics fields as sanitary products (e.g. disposable diapers) and humectants. These hydrogels are primarily made of poly(sodium acrylate) based materials. Used hydrogels are disposed of by incineration, so if they are treated massively, the temperature in the incinerator will drop to cause a potential problem of producing dioxins. Attempts are therefore being made to use hydrogels that decompose in the soil to exert no environmental impact, as exemplified by poly(sodium glutamate) and poly(sodium aspartate) having irradiation-generated crosslinks.

Formaldehyde and glutaraldehyde are conventionally used to create chemical crosslinks in chitin and chitosan. However, since the aldehydes contaminate the working environment or the residual aldehydes may irritate the skin, a safer method of crosslinking is desired.

Hydrogels produced by crosslinking water-soluble polymers absorb a large amount of water, so they are used in sanitary products such as disposable diapers. Typically, zeolite incorporating antimicrobes such as silver are added as an antimicrobial agent. However, accumulation of silver is not preferred from the viewpoint of health. It is therefore required to develop high-molecular weight polymers that themselves have antimicrobial activity.

Chitosan has positive electric charges, so they bind to negatively charged microorganisms and exhibit antimicrobial activity to inhibit microbial growth. Thus, the applicable scope of chitin and chitosan which are currently discarded will expand and their added value will further increase if a safer method of their crosslinking is found and if hydrogels that themselves have antimicrobial activity are developed. However, chitin and chitosan have no compatible solvents and if they are irradiated in a solid state, marked decomposition will occur. Therefore, chitin and chitosan are difficult to process into films or fibers and it is also difficult to crosslink them by radiation.

If the hydrogen in hydroxyl groups in chitin and chitosan is replaced by a hydroxyl or carboxyl group, intermolecular hydrogen bonds sufficiently weaken that chitin and chitosan will come to dissolve in water. As a result of their intensive studies, the present inventors found that carboxymethylated chitin and chitosan (chitin and chitosan derivatives) could be crosslinked when irradiated in a thick paste form. The present invention has been accomplished on the basis of this finding. It was also revealed that CM-chitosan was a hydrogel having a unique feature of presenting antimicrobial activity.

SUMMARY OF THE INVENTION

Water-soluble chitin and chitosan derivatives, when exposed to radiation either in a solid state or as a dilute ($\leqq 5\%$) aqueous solution, preferentially undergo decomposition, so it has been difficult to process them by radiation-induced crosslinking. The present inventors added purified water to chitin and chitosan derivatives and kneaded them well to prepare a thick paste and successfully crosslinked the paste by applying an ionizing radiation. Interestingly, the hydrogel of CM-chitosan derivative obtained by crosslinking has antimicrobial activity.

DETAILED DESCRIPTION OF THE INVENTION

Figure 1:
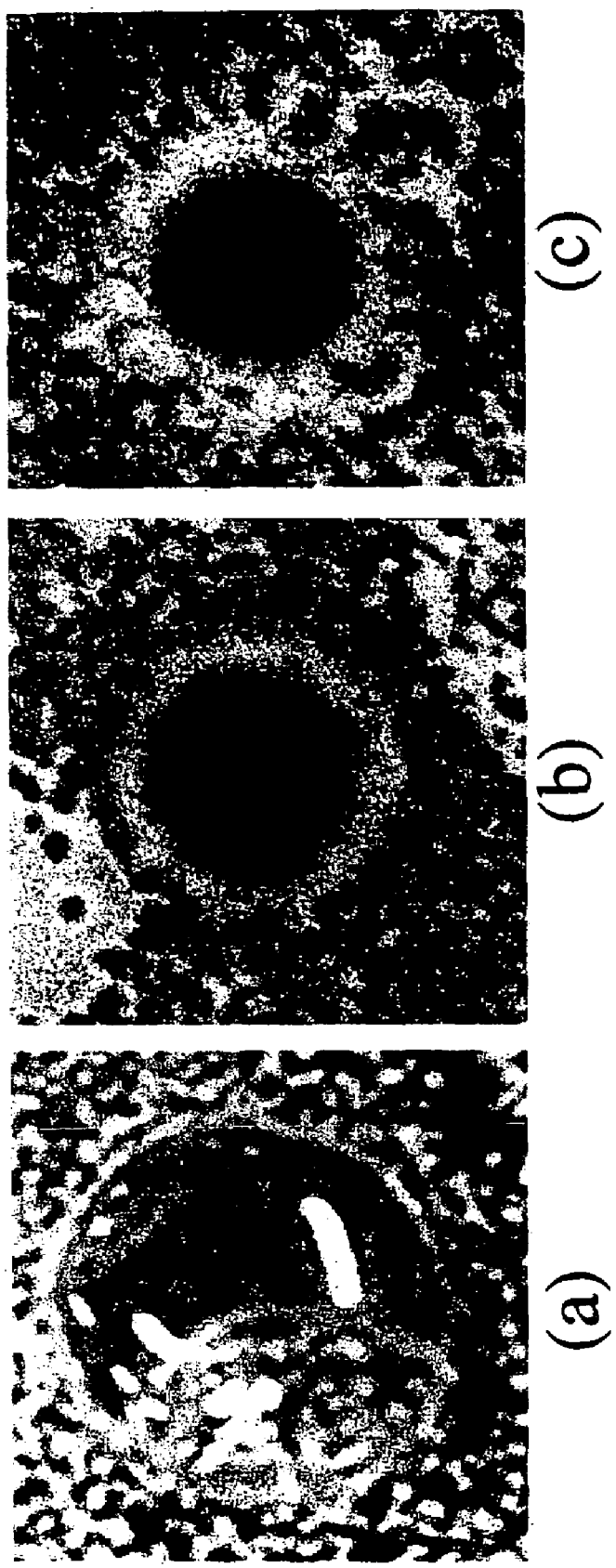
FIG. 1A is a photo showing that a PVA hydrogel has no antimicrobial activity against *E. coli;*
FIG. 1B is a photo showing the antimicrobial activity of a CM-chitosan hydrogel with a gel fraction of 40% against *E. coli*.
FIG. 1C is a photo showing the antimicrobial activity of a CM-chitosan hydrogel with a gel fraction of 25% against *E. coli.*

The hydrogels of chitin and chitosan derivatives according to the invention are synthesized by the following method. Chitin and chitosan derivatives having different degrees of substitution are kneaded well with purified water to make a concentrated paste that is thick enough not to flow out if the container is tilted. The paste is a mixture of 100 parts by weight of derivative and 3 to 1,000 parts by weight of purified water. The paste is put into a poly(vinylidene chloride) bag, evacuated, heat sealed and exposed to electron beams. Before irradiation, the paste was soft but upon irradiation, it turned to a rubbery and elastic gel. In order to perform radiation-induced crosslinking, the paste must have a concentration of at least 10%, preferably between 30% and 50%. In a solid state or at concentrations lower than 10%, decomposition occurs preferentially and there is no visible gel formation by crosslinking. Solubility in water varies with the degree of substitution and the higher the substitution, the thicker the paste that can be prepared and the faster its preparation. Preferably, a total of at least 20 hydroxgel groups and carboxyl groups in the derivative starting material form an alkali metal salt, an ammonium salt, or an amine salt.

The ionizing radiation can be γ-rays, electron beams or X-rays. The crosslinking dose is 0.5~1,000 kGy, preferably 5~300 kGy.

Any chitin and chitosan derivatives that are soluble in water can be used in the invention. the derivatives have an average degree of substitution of at least 0.01. Higher degrees of substitution are preferred since they increase the affinity for water and, hence, provide thicker pastes. The most preferred degree of substitution is 0.3~0.9. Chitin is extracted from the outer covering of crustaceans such as shrimps and crabs by deproteinization and chitosan is obtained from chitin by deacetylation. Since chitin and chitosan are comparatively cheap materials, they are preferred as materials for the synthesis of derivatives.

Examples of the chitin derivatives of the invention include CM-chitin, carboxyethyl-chitin, methyl-chitin, ethyl-chitin, hydroxyethyl-chitin, hydroxypropyl-chitin, oxidized chitin, acetyl-chitin, aminoalkyl-chitin and allyl-chitin. Examples of the chitosan derivatives of the invention include CM-chitosan, carboxyethyl-chitosan, methyl-chitosan, ethyl-chitosan, hydroxyethyl-chitosan, hydroxypropyl-chitosan, oxidized chitosan, acetyl-chitosan, aminoalkyl-chitosan and allyl-chitosan.

For the purpose of industrial production, two preferred examples of the ionizing radiation are γ-rays from cobalt-60 and electron beams from an accelerator. The most preferred electron accelerator is one of medium to high energy types that have acceleration voltages of at least 1 MeV and can irradiate thick sheets. If a yet-to-be irradiated sample is pressurized to form a film, even the electron beams from a low-energy electron accelerator having an acceleration voltage of less than 1 MeV can penetrate the sample and the intended gel can be formed by radiation-induced crosslinking. During irradiation, oxygen has little effect on crosslinking; however, in order to ensure that water will not evaporate and the density of crosslinks will not decrease during irradiation, the top surface of the sample is desirably covered with a film of plastics such as polyester.

Gel fraction is determined as follows. The gel formed by irradiation is freeze-dried and put into a vacuum dryer where it is dried at 50° C. until its weight becomes constant. The dried sample is put into a cage of stainless steel wire having a fineness of 200 mesh and immersed in a large volume of water for 48 hours. The uncrosslinked soluble component of the sample has moved into the aqueous phase, leaving only the gelled component in the cage. The stainless steel cage holding the gel is immersed in methanol for 1 hour, recovered and then dried at 50° C. for 24 hours. Gel fraction is calculated by the following equation:

Gel fraction(%)=(gel weight without soluble component/initial dry weight)×100

To determine the degree of swell, an irradiated paste of sample is immersed in a large volume of water for 48 hours and the obtained gel is freeze-dried and immersed in purified water; the degree of swell is expressed in grams of the purified water absorbed by one gram of the dry gel. Hydrogel produced in accordance with the method of the invention holds at least 14 grams of water per gram of dry gel.

The antimicrobial activity of the hydrogel is determined as follows. An irradiated paste of sample is immersed in purified water for 48 hours in order to remove the uncrosslinked sol. The remaining gel is cut to a specified size and put into a Petri dish containing an agar medium plated with *E. coli*. As time passes, *E. coli* grows. A clear zone forming around the hydrogel indicates an inhibition of *E. coli* growth and one may conclude that the hydrogel has antimicrobial activity.

Chitosan has antimicrobial activity whose intensity increases if the molecular weight of chitosan is decreased by irradiation. However, chitosan dissolves only in dilute acids and cannot be easily processed into hydrogel or sheet. According to the invention, a hydrogel having antimicrobial activity could successfully be produced from chitosan derivatives by crosslinking them with radiation. By radiation-induced crosslinking, the hydrogel can be obtained in blocks, sheets or various other shapes and may find use in the following applications.

In the medical field, the hydrogel of chitosan derivatives or their blends with other hydrogels may be used as wound dressings that are applied to cover wounds due to injury or burn and promote their healing. Wound dressings of wet type have recently been put on the market since burn and wounds such as bedsores of the elderly can heal rapidly in a wet environment and the healed wound has a smooth surface. The wound dressing using the hydrogel of chitosan derivatives according to the invention is different from the conventional wet type wound dressing since the hydrogel itself has antimicrobial activity and there is no need to add any antimicrobes.

The antimicrobial hydrogel of the invention can be gel spun into fibers having antimicrobial activity. The hydrogel may be deprived of water by evaporation and can subsequently be shaped into a film, which is attached to the surfaces of various substrates to thereby make antimicrobial articles that can prevent the growth of molds and other deleterious microorganisms. Thus, the antimicrobial hydrogel of the invention has potential application in various fields.

The following examples and comparative examples are provided for further illustrating the present invention.

EXAMPLE 1

CM-chitin was used; it had a degree of substitution of 0.49, a molecular weight of $2.82 \times 10^4$ and a degree of deacetylation of 17.7%. It was kneaded well with varying volumes of purified water to make samples in paste (grease) form at concentrations of 10, 20, 30, 40 and 50%, which were irradiated with electron beams to a dose of 50 kGy. The results are shown in Table 1, from which it is clear that by irradiating the paste, a water-insoluble gel formed and crosslinking occurred. Upon immersion in a large volume of water, the crosslinked CM-chitin swelled to form a hydrogel. For crosslinking, the CM-chitin preferably has a concentration of 20~40%.

TABLE 1

Gel fractions and the degrees of swell in the case of exposing 50 kGy of electron beams to CM-chitin (degree of substitution: 0.49) at varying concentrations

| | Concentration (%) of CM-chitin | | | | |
|---|---|---|---|---|---|
| | 10 | 20 | 30 | 40 | 50 |
| Gel fraction (%) | 31 | 48 | 50 | 52 | 28 |
| Degree of swell (g $H_2O$/1 g dry gel) | 111 | 56 | 34 | 21 | 93 |

EXAMPLE 2

CM-chitin was used; it had a degree of substitution of 0.83, a molecular weight of $2.93 \times 10^4$ and a degree of deacetylation of 31.4%. It was kneaded well with varying volumes of purified water to make samples in paste (grease) form at concentrations of 10, 20, 30, 40 and 50%, which were irradiated with electron beams to a dose of 50 kGy. The results are shown in Table 2, from which it is clear that by irradiating the paste, a water-insoluble gel formed and crosslinking occurred. Upon immersion in a large volume of water, the crosslinked CM-chitin swelled to form a hydrogel. For crosslinking, the CM-chitin preferably has a concentration of 20~40%.

TABLE 2

Gel fractions and the degrees of swell in the case of exposing 50 kGy of electron beams to CM-chitin (degree of substitution: 0.83) at varying concentrations

| | Concentration (%) of CM-chitin | | | | |
|---|---|---|---|---|---|
| | 10 | 20 | 30 | 40 | 50 |
| Gel fraction (%) | 41 | 52 | 59 | 61 | 46 |
| Degree of swell (g H$_2$O/1 g dry gel | 148 | 58 | 20 | 14 | 120 |

COMPARATIVE EXAMPLE 1

Two kinds of CM-chitin were used; one of them had a degree of substitution of 0.49, a molecular weight of $2.82 \times 10^4$ and a degree of deacetylation of 17.7%; the other had a degree of substitution of 0.83, a molecular weight of $2.93 \times$ and a degree of deacetylation of 31.4%. Each sample was exposed to electron beams from an accelerator in two states, solid at room temperature and as a dilute ($\leqq 5\%$) aqueous solution, until the dose was 200 kGy. In either case, the molecular weights of the samples decreased to such an extent that they were readily soluble in water; however, no water-insoluble gel component formed and no crosslinking occurred under the conditions employed.

EXAMPLE 3

CM-chitosan was used; it had a degree of substitution of 0.91, a molecular weight of $3.1 \times 10^4$ and a degree of deacetylation of 84.0%. It was kneaded well with varying volumes of purified water to make samples in paste (grease) form at concentrations of 20, 25, 35 and 50%, which were irradiated with electron beams to a dose of 100 kGy. The results are shown in Table 3, from which it is clear that by irradiating the paste, a water-insoluble gel formed and crosslinking occurred. Upon immersion in a large volume of water, the crosslinked CM-chitin swelled to form a hydrogel. For crosslinking, the CM-chitosan preferably has a concentration of 25~35%.

A test was conducted to evaluate the antimicrobial activity of a CM-chitosan hydrogel that was prepared by exposing electron beams to a paste of 35% CM-chitosan to a dose of 150 kGy. The sample was immersed in purified water for 48 hours to remove the sol which was a soluble component. The thus prepared CM-chitosan hydrogel had a gel fraction of 40%.

The hydrogel was cut to a disk with a diameter of 10 mm and placed on an agar medium plated with $1 \times 10^6$ E. coli cells/mL which were cultured at 37° C. As FIG. 1B shows, a clear zone about 5 mm wide formed around the hydrogel by inhibiting the growth of E. coli; the CM-chitosan hydrogel obviously had antimicrobial activity.

TABLE 3

Gel fractions and the degrees of swell in the case of exposing 100 kGy of electron beams to CM-chitosan at varying concentrations

| | Concentration (%) of CM-chitosan | | | |
|---|---|---|---|---|
| | 20 | 25 | 35 | 50 |
| Gel fraction (%) | 36 | 40 | 41 | 43 |
| Degree of swell (g H$_2$O/1 g dry gel | 126 | 86 | 58 | 117 |

EXAMPLE 4

CM-chitosan was used; it had a degree of deacetylation of 84.0%, a degree of substitution (degree of carboxymethylation) of 0.91 and a viscosity average molecular weight of $3.1 \times 10^4$. A CM-chitosan hydrogel was prepared by exposing electron beams to a paste of 35% CM-chitosan to a dose of 80 kGy. The sample was immersed in purified water for 48 hours to remove the sol which was a soluble component. The thus prepared CM-chitosan hydrogel had a gel fraction of 25%.

As in Example 3, the hydrogel was cut to a disk with a diameter of 10 mm and placed on an agar medium plated with $1 \times 10^6$ E. coli cells/mL which were cultured at 37° C. As FIG. 1C shows, a clear zone about 5 mm wide formed around the hydrogel by inhibiting the growth of E. coli. Growth of E. coli occurred in areas of the medium other than around the hydrogel disk.

COMPARATIVE EXAMPLE 2

CM-chitosan was used; it had a degree of substitution of 0.91, a molecular weight of $3.1 \times 10^4$ and a degree of deacetylation of 84.0%. The sample was exposed to electron beams from an accelerator in two states, solid at room temperature and as a dilute ($\leqq 10\%$) aqueous solution, until the dose was 300 kGy. In either case, the molecular weight of the sample decreased to such an extent that it was readily soluble in water; however, no water-insoluble gel component formed and no crosslinking occurred under the conditions employed.

COMPARATIVE EXAMPLE 3

A hydrogel prepared by irradiating an aqueous solution of 10% poly(vinyl alcohol) was tested for its antimicrobial activity. A disk of the PVA hydrogel with a diameter of 10 mm was placed on an agar medium plated with $1 \times 10^6$ E. coli cells/mL which were cultured at 37° C. As FIG. 1A shows, E. coli grew uniformly around the hydrogel with the lapse of time. No clear zone formed around the hydrogel, clearly demonstrating the absence of its antimicrobial activity. The white bands in the center of FIG. 1A are due to the reflection of light from the clear hydrogel that occurred when the picture was taken.

Speaking of potential applications of the invention, the CM-chitin has acetyl groups, so after being crosslinked, it can be reacted with such acetyl groups to create a hydrogel having a new property. The CM-chitosan hydrogel is a unique gel which itself has antimicrobial activity. In the medical field, the CM-chitosan hydrogel can be used as a wound dressing which, when applied to a wound, can prevent the ingress of germs to promote the healing of the wound. The CM-chitosan can also be employed in preventing the putrefaction of water and in the production of antimicrobial fibers.

What is claimed:

1. A process for producing a hydrogel of a chitin derivative having a crosslinked structure, comprising adding purified water to a water-soluble chitin derivative, kneading the resulting mixture to prepare a concentrated paste having a concentration of 30% to 50% which is thick enough not to flow out if the container is tilted, and irradiating the concentrated paste with an ionizing radiation to a dose of 5 to 300 kGy to obtain a water-insoluble gel of the chitin derivative having a crosslinked structure which is swelled upon immersion in a large volume of water to form a hydrogel and absorbs water in a volume at least 5 times as much as its own weight, wherein said chitin derivative is selected from the group consisting of carboxymethyl-chitin, carboxyethyl-chitin, methyl-chitin, ethyl-chitin, hydroxyethyl-chitin, hydroxypropyl-chitin, oxidized chitin, acetyl-chitin, aminoalkyl-chitin, allyl-chitin, and blends thereof.

2. The process according to claim 1, wherein a total of at least 20 hydroxyl groups or carboxyl groups in the chitin derivative as the starting material forms an alkyl metal salt, an ammonium salt or an amine salt.

3. A process for producing hydrogel of a chitin derivative having a crosslinked structure, comprising adding purified water to a water-soluble chitin derivative, kneading the resulting mixture to prepare a concentrated paste having a concentration of 30% to 50%, and irradiating the concentrated paste with an ionizing radiation to a dose of 5 to 300 kGy to obtain a water-insoluble gel of the chitin derivative having a crosslinked structure, wherein said chitin derivative is selected from the group consisting of carboxymethyl-chitin, carboxyethyl-chitin, methyl-chitin, ethyl-chitin, hydroxyethyl-chitin, hydroxypropyl-chitin, oxidized chitin, acetyl-chitin, aminoalkyl-chitin, allyl-chitin, and blends thereof.

4. The process according to claim 3, wherein a total of at least 20 hydroxyl groups or carboxyl groups in the chitin derivative as the starting material forms an alkyl metal salt, an ammonium salt or an amine salt.

* * * * *